US00PP13654P2

(12) United States Plant Patent
Hill, Jr.

(10) Patent No.: US PP13,654 P2
(45) Date of Patent: Mar. 11, 2003

(54) GUZMANIA PLANT NAMED 'ESQUIRE'

(75) Inventor: Herbert H. Hill, Jr., Lithia, FL (US)

(73) Assignee: Twyford International Inc., Santa Paula, CA (US)

( * ) Notice: Subject to any disclaimer, the term of this patent is extended or adjusted under 35 U.S.C. 154(b) by 0 days.

(21) Appl. No.: 10/158,967

(22) Filed: May 31, 2002

(51) Int. Cl.[7] ..... A01H 5/00
(52) U.S. Cl. ..... Plt./371
(58) Field of Search ..... Plt./371

*Primary Examiner*—Kent Bell
(74) *Attorney, Agent, or Firm*—C. A. Whealy

(57) ABSTRACT

A new and distinct cultivar of Guzmania plant named 'Esquire', characterized by it upright and outwardly arching plant habit; small stature; dark green-colored foliage that is flushed or streaked with purple; inflorescences held upright and above foliage on strong scapes; inflorescences with closely-spaced bright red-colored flower bracts and tipped with white; and long-lasting inflorescences that maintain good coloration for about two to three months in an interior environment.

1 Drawing Sheet

BOTANICAL CLASSIFICATION/CULTIVAR DESIGNATION

Guzmania hybrid cultivar 'Esquire'.

BACKGROUND OF THE INVENTION

The present Invention relates to a new and distinct cultivar of Guzmania plant, botanically known as Guzmania hybrid, and hereinafter referred to by the cultivar name 'Esquire'.

Guzmania is native to tropical America. Leaves of the Guzmania are usually formed as basal rosettes which are stiff and arranged in several vertical ranks. Guzmania have terminal flower spikes or panicles which are often bracted with petals united in a tube about as long as the calyx.

The new Guzmania is a product of a planned breeding program conducted by the Inventor in Lithia, Fla. The objective of the breeding program is to create new Guzmania cultivars with a plant habit appropriate for container production, desirable flowering habit and inflorescence coloration, and good postproduction longevity.

The new Guzmania originated from a cross-pollination made by the Inventor in Lithia, Fla. in March, 1994, of the *Guzmania lingulata* cultivar 'El Cope', not patented, as the female, or seed, parent with the Guzmania hybrid cultivar 'Anita', not patented, as the male, or pollen, parent. The cultivar Esquire was discovered and selected by the Inventor as a flowering plant within the progeny of the stated cross-pollination in a controlled environment in Lithia, Fla., in April, 1996.

Asexual reproduction of the new Guzmania by off-shoots in a controlled environment in Lithia, Fla. since June, 1997, has shown that the unique features of this new Guzmania are stable and are reproduced true to type in successive generations. Asexual reproduction of the new Guzmania by tissue culture done in a laboratory in Sebring, Fla. since January, 1998, has also confirmed that the unique features of this new Guzmania are stable and are reproduced true to type in successive generations.

SUMMARY OF THE INVENTION

The new Guzmania has not been observed under all possible environmental conditions. The phenotype may vary somewhat with variations in environment such as temperature and light intensity without, however, any variance in genotype.

The following characteristics have been repeatedly observed and are determined to be basic characteristics of 'Esquire' and distinguish 'Esquire' as a new and distinct cultivar of Guzmania:

1. Upright and outwardly arching plant habit; small stature, suitable for 10 to 12-cm containers.
2. Dark green-colored foliage that is flushed or streaked with purple on both upper and lower surfaces.
3. Inflorescences held upright and above foliage on strong scapes.
4. Inflorescences with closely-spaced bright red-colored flower bracts; terminal bracts are tipped with white.
5. Long-lasting inflorescences that maintain good coloration for about two to three months in an interior environment.

Plants of the new Guzmania differ from plants of the female parent, the cultivar El Cope, in the following characteristics:

1. Plants of the new Guzmania grow more rapidly and are easier to grow than plants of the cultivar El Cope.
2. Plants of the new Guzmania are much smaller than plants of the cultivar El Cope.
3. Plants of the new Guzmania have shorter, thinner, more upright and more flexible leaves than plants of the cultivar El Cope.
4. Plants of the new Guzmania are more tolerant to stress than plants of the cultivar El Cope.

Plants of the new Guzmania differ from plants of the male parent, the cultivar Anita, in the following characteristics:

1. Plants of the new Guzmania have shorter inflorescences than plants of the cultivar Anita.
2. Primary flower bracts of plants of the new Guzmania are more closely spaced than primary flower bracts of plants of the cultivar Anita.

3. Plants of the new Guzmania have more terminal flower bracts than plants of the cultivar Anita.
4. Plants of the new Guzmania have red-colored flower bracts whereas plants of the cultivar Anita have orange-colored flower bracts.

Plants of the new Guzmania can be compared to plants of the Guzmania cultivar Empire, not patented. In side-by-side comparisons conducted in Lithia, Fla., plants of the new Guzmania differed from plants of the cultivar Empire in the following characteristics:

1. Leaves of plants of the new Guzmania were dark green in color and flushed or streaked with purple whereas leaves of plants of the cultivar Empire were light to medium green in color.
2. Plants of the new Guzmania had larger inflorescences than plants of the cultivar Empire.
3. Primary flower bracts of plants of the new Guzmania were longer, narrower, and more pointed than primary flower bracts of plants of the cultivar Empire.

BRIEF DESCRIPTION OF THE PHOTOGRAPH

The accompanying colored photograph illustrates the overall appearance of the new Guzmania, showing the colors as true as it is reasonably possible to obtain in colored reproductions of this type. Colors in the photograph may differ slightly from the color values cited in the detailed botanical description which accurately describe the colors of the new Guzmania. The photograph comprises a side perspective view of a typical flowering plant of 'Esquire' grown in a container.

DETAILED BOTANICAL DESCRIPTION

The aforementioned photograph and following observations and measurements describe plants grown in Lithia, Fla., under a polyethylene-covered greenhouse and conditions which closely approximate those used in commercial practice. During the production of the plants, day temperatures ranged from 70 to 90° F., night temperatures ranged from 65 to 75° C., and light levels were about 1,500 to 2,000 foot-candles. Single plants used for the photograph and for the description were about 12 months old and grown in 12-cm containers. Color references are made to The Royal Horticultural Society Colour Chart, 1996 Edition, except where general terms of ordinary dictionary significance are used.

Botanical classification: Guzmania hybrid cultivar Esquire.

Parentage:

*Female, or seed, parent.*—*Guzmania lingulata* cultivar El Cope, not patented.

*Male, or pollen, parent.*—Guzmania hybrid cultivar Anita, not patented.

Propagation:

*Type.*—By tissue culture.

*Time to initiate roots on tissue-cultured plants.*—Summer: About 14 days at day temperatures of 70 to 90° F. and night temperatures of 65 to 75° F. Winter: About 14 to 18 days at day temperatures of 70 to 90° F. and night temperatures of 65 to 75° F.

*Time to produce a rooted tissue-cultured plant.*—Summer: About 140 days at day temperatures of 70 to 90° F. and night temperatures of 65 to 75° F. Winter: About 150 days at day temperatures of 70 to 90° F. and night temperatures of 65 to 75° F.

*Root description.*—Fine, wiry; initially greenish white becoming brown in color.

Plant description:

*General appearance.*—Upright and outwardly arching plant habit. Closely layered strap-like leaves arranged in a basal rosette. Appropriate for 10 to 12-cm containers. Vigorous growth habit. Plant height, soil surface to top of inflorescence: About 28 to 31 cm.

*Plant diameter or spread.*—About 56 to 58 cm.

*Foliage description.*—Arrangement: Basal rosette, spiral phyllotaxis; sessile. Quantity of leaves per plant: Plants typically produce about 30 leaves before inflorescence development. Shape: Ligulate. Apex: Acute. Margin: Entire. Length: About 35 to 40 cm. Width: About 2 to 2.5 cm; width at base, about 5 cm. Aspect: Blade, channeled; leaves curved downward towards the apex. Texture, upper and lower surfaces: Leathery, stiff; glabrous. Venation: Parallel. Leaf sheath: Not observed. Color: Young and fully expanded leaves, upper surface: Darker than, but closest to 137A; towards the base, striations of 187A to 187B. Young and fully expanded leaves, lower surface: Darker and more green than, but closest to 146B; flushed and striated with 187A, striations most prominent towards the base. Venation, upper and lower surfaces: Same as lamina.

Inflorescence description:

*Inflorescence form.*—Terminal inflorescences supported on erect and strong scapes.

*Inflorescence longevity.*—Inflorescences of the new Guzmania are very long-lasting; bract coloration is maintained for at about two to three months in an interior environment. Inflorescences persistent.

*Natural flowering season and time to flower.*—Plants flower throughout the year and begin to flower about 13 to 16 weeks after floral induction.

*Flowers.*—Arrangement: Single flowers, one flower per terminal bract. Quantity per inflorescence: About 40 flowers or flower buds, flowers terminal in the inflorescence concealed by bracts. Corolla: Arrangement: Three petals, gameopetalous. Length: About 4.4 cm. Width: About 4 mm. Color: 155D. Calyx: Arrangement: Three petals, gameosepalous. Length: About 2.8 cm. Width: About 7 mm. Color: 155B. Reproductive organs: Stamens: Quantity per flower: Six. Filament length: About 2.6 cm. Anther length: About 4 mm. Anther color: Brownish black. Pistils: Style length: About 3.2 cm. Style color: 145D. Ovary: Superior with three locules. Length: About 9 mm. Color: 145D.

*Bracts.*—Arrangement: Terminal bracts at the terminal, subtended by primary bracts, and scape bracts spirally clasp the scape. Quantity per flower spike, terminal bracts: About 40. Quantity per flower spike, primary bracts: About 12. Quantity per flower spike, scape bracts: About 8. Shape, terminal bracts: Ovate with bluntly rounded apices; margin, entire. Shape, primary bracts: Ovate with acutely tapered apices; margin, entire. Shape, scape bracts: Laneolate with acute apices; margins, entire. Length, terminal bracts: About 5.8 cm. Width, terminal bracts: About 2.4 cm. Length, primary bracts: About 7.5 to 10.5 cm. Width, primary bracts: About 1.5 to 2.2 cm. Length, scape bracts: About 11 to 19 cm. Width, scape bracts: About 1.5 to 2.4 cm. Texture, all bracts, upper and lower surfaces: Leathery; smooth. Color:

Terminal bracts, upper and lower surfaces: 42A; apex, 155D; towards the base, 157D. Primary bracts, upper and lower surfaces: 46A to 46B; apex, 46A to 187A; towards the base, 157D. Scape bracts, upper and lower surfaces: Upper scape bracts, 46A; lower scape bracts, similar to leaf coloration.

*Scape.*—Strength: Strong. Aspect: Typically erect. Length: About 24 cm. Diameter: About 1 cm. Texture: Smooth. Color: 155B.

*Seed/fruit.*—Seed and fruit production has not been observed.

Temperature tolerance: Plants of the new Guzmania have been observed to tolerate temperatures from about 50 to 100° F.

Disease/pest resistance: Plants of the new Guzmania have not been observed to resistant to pathogens and pests common to Guzmania.

It is claimed:

1. A new and distinct cultivar of Guzmania plant named 'Esquire', as illustrated and described.

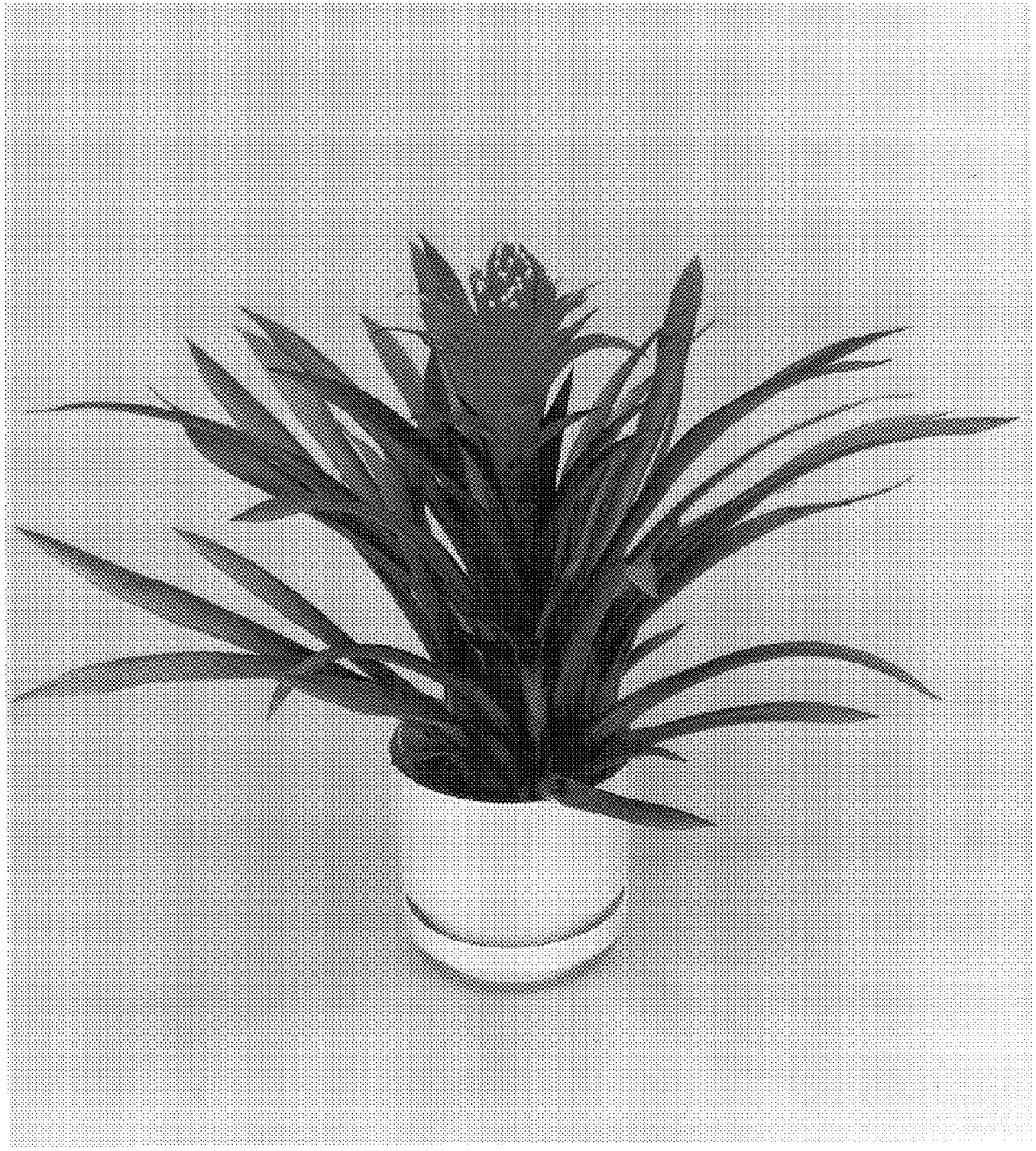

* * * * *